United States Patent [19]
Cicha

[11] Patent Number: 6,037,598
[45] Date of Patent: Mar. 14, 2000

[54] ARRANGEMENT ON AN ULTRAVIOLET STERILIZATION SYSTEM

[75] Inventor: John Cicha, Shoreview, Minn.

[73] Assignee: Tetra Laval Holdings & Finance, SA, Pully, Switzerland

[21] Appl. No.: 09/014,987

[22] Filed: Jan. 28, 1998

[51] Int. Cl.[7] .............................. A61L 2/10; H05B 41/00; G01N 23/00
[52] U.S. Cl. ................. 250/455.11; 315/DIG. 2
[58] Field of Search ................. 250/455.11; 315/DIG. 2

[56] References Cited

U.S. PATENT DOCUMENTS

| | | |
|---|---|---|
| 5,259,169 | 11/1993 | Appelbaum et al. .................. 53/373.8 |
| 5,606,169 | 2/1997 | Hiller et al. ........................ 250/455.11 |
| 5,788,940 | 8/1998 | Cicha et al. ............................... 422/24 |
| 5,828,186 | 10/1998 | Slegers et al. ........................... 315/290 |

*Primary Examiner*—Edward P. Westin
*Assistant Examiner*—Nikita Wells
*Attorney, Agent, or Firm*—Welsh & Katz, Ltd.

[57] ABSTRACT

An arrangement for an ultraviolet sterilization system disposed on a packaging machine for processing a series of cartons is disclosed herein. The system may have an ignitor for expediting the commencement of the ultraviolet lamp. Additionally, the system may have an ultraviolet monitor for monitoring the intensity of the ultraviolet radiation being directed to a series of cartons being processed on the packaging machine. The monitor will alert an operator to a change in the intensity of the ultraviolet radiation thereby ensuring properly sterilized cartons.

7 Claims, 7 Drawing Sheets

D=Ballast Conn.
L=Line Conn.
N=Neutral Conn.

ARRANGEMENT ON AN ULTRAVIOLET STERILIZATION SYSTEM

CROSS REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention generally relates to a UV sterilization system. Specifically, the present invention is directed toward a UV sterilization system utilized within a linear form, fill and seal packaging machine.

2. Description of the Related Art

The sterilization of packaging containers such as gable-top cartons, has been accomplished through irradiation with ultraviolet ("UV") energy. In such a sterilization system, an UV lamp is mounted above the conveyor line of a packaging machine. The UV lamp irradiates the container as the container passes below the UV lamp, usually just prior to filling of the container with a flowable food product such as milk.

In order to have an effective kill of microorganisms, the UV energy must meet a minimum level of watts/$cm^2$-sec. The disinfection of the cartons depends on the combination of intensity of UV radiation and exposure time (dose). If during the conveyance of containers under the UV lamp, the intensity of the UV lamp is below the minimum level, then the containers may not receive a sufficient amount of UV energy and may not be properly sterilized. The operator would have no knowledge of such non-sterilization, thus possibly resulting in the distribution of a contaminated container to the public. More likely, the operator would eventually notice the lack of intensity, and the entire batch would have to be discarded since the operator would be unable to detect exactly when the intensity decreased below the minimum level. Such a scenario would prove economically painful to a dairy, or other food packager.

Another operational problem associated with UV sterilization systems is starting the UV lamp in a cold environment. In a mercury UV lamp, it is the heating and vaporization of the mercury which creates the UV radiation. Contained within the shell of the UV lamp is the mercury and an inert gas. An anode is at one end of the UV lamp and a cathode is at the other end of the UV lamp. When a sufficient voltage is delivered to the UV lamp, an arc is struck across the UV lamp. If the temperature is too cold, under 8° C., then the voltage from a power supply may be insufficient to strike an arc across the UV lamp. Also, it is often the case that the UV lamp must be shut down during a product run to provide repair or correct a problem on the line. The problem does not need to be associated with the UV lamp to necessitate its inactivation. When such a shut down occurs, the downtime is further amplified by the added start-up time for the UV lamp. The reason for the increased downtime arises from the necessity of having to wait for the vaporized mercury to cool down and have sufficient condensation to again create an arc across the UV lamp. Too much mercury in the vapor phase within the UV lamp shell will interfere with the striking of an arc between the anode and cathode via the inert gas, thus, an operator must wait for the mercury to condense in order to strike an arc in the UV lamp, and restart the UV lamp.

Resolution of these problems would further enhance the efficiencies of dairies, juice packagers, and other flowable food packagers who utilize form, fill and seal packaging machines having sterilization features, and in particular those facilities in cold environments.

BRIEF SUMMARY OF THE INVENTION

The present invention resolves many of the problems of the prior art by providing a UV system that monitors the intensity of the UV lamp and warns an operator of any variation in the intensity. The present invention also provides an UV system with an ignitor to strike an arc across an UV lamp in cold weather and during restart operations.

It is a primary object of the present invention to provide means for monitoring the intensity of radiation from an ultraviolet lamp disposed on a linear form, fill and seal packaging machine.

It is an additional object of the present invention to provide an ignitor for expediting the starting of an ultraviolet lamp from an inactive state.

It is an additional object of the present invention to provide means for alerting an operator of a change in the intensity of a ultraviolet lamp during sterilization of containers on a linear form, fill and seal packaging machine.

Having briefly described this invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

Several features of the present invention are further described in connection with the accompanying drawings in which:

There is illustrated in FIG. 1 a schematic side view of a linear form, fill and seal packaging machine;

Figure 2:
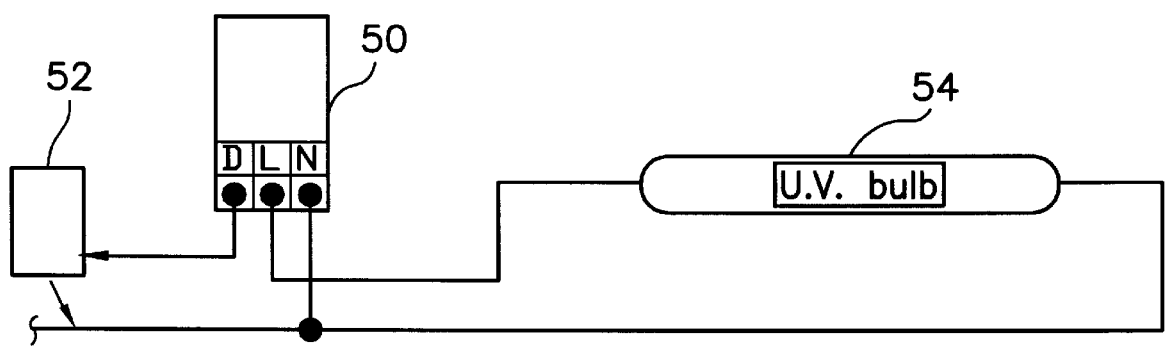
Figure 3:
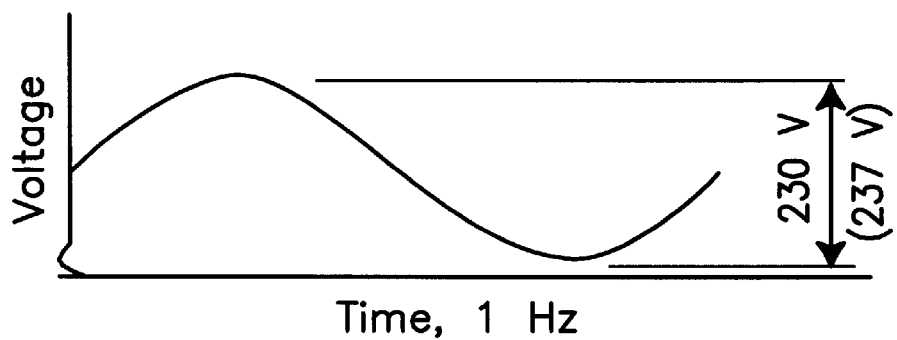
Figure 4:
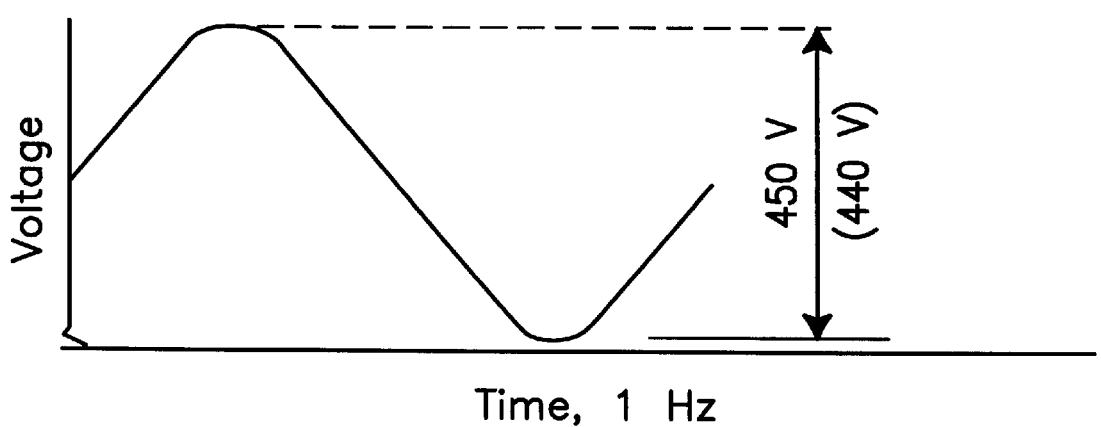
Figure 5:
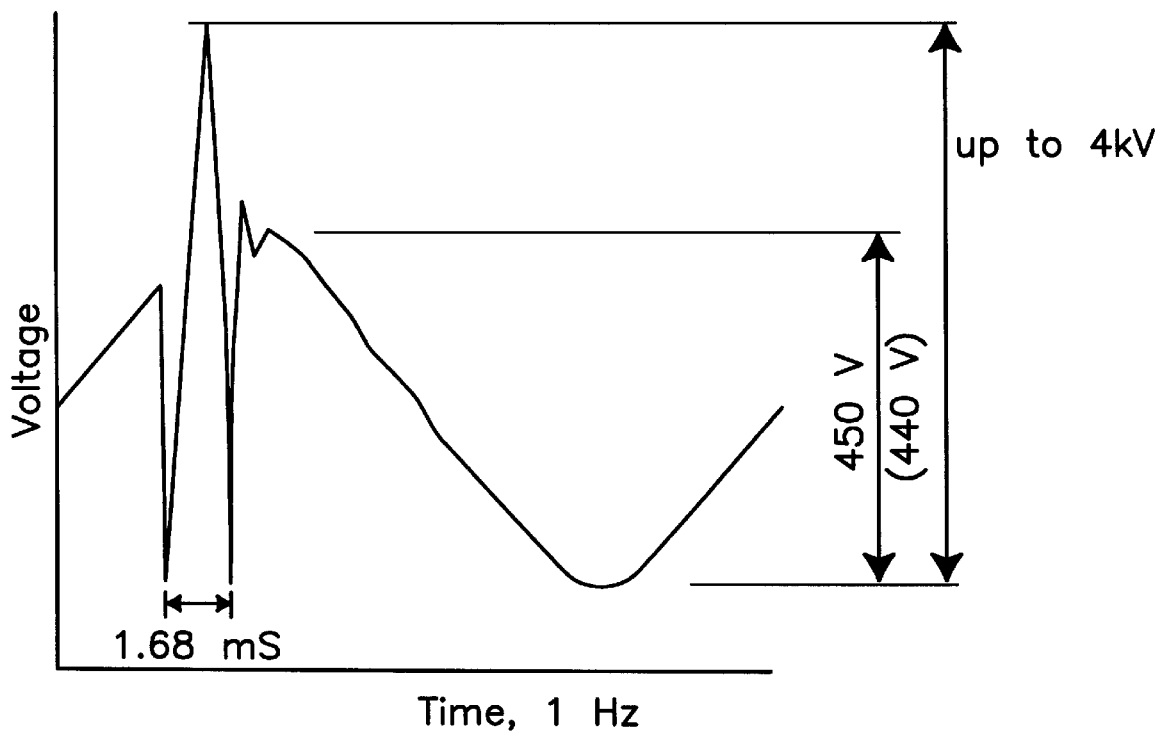
Figure 6:
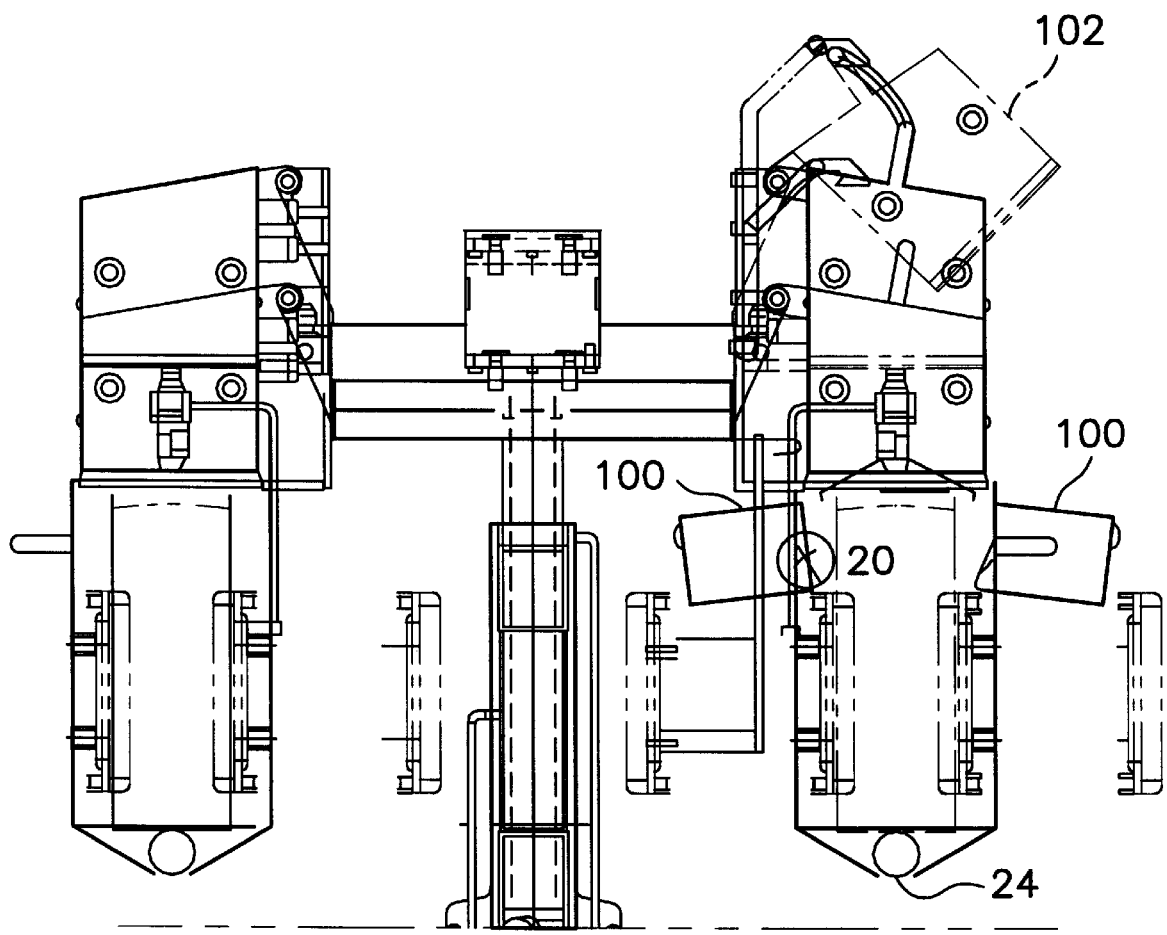
Figure 8:
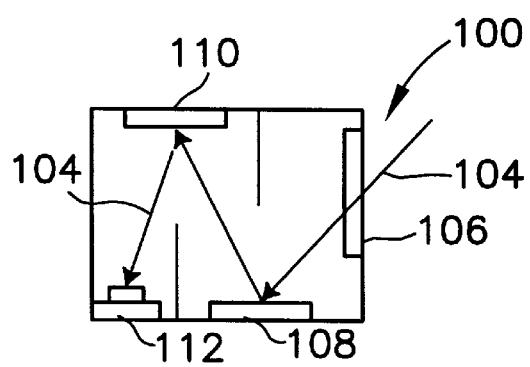
Figure 7:
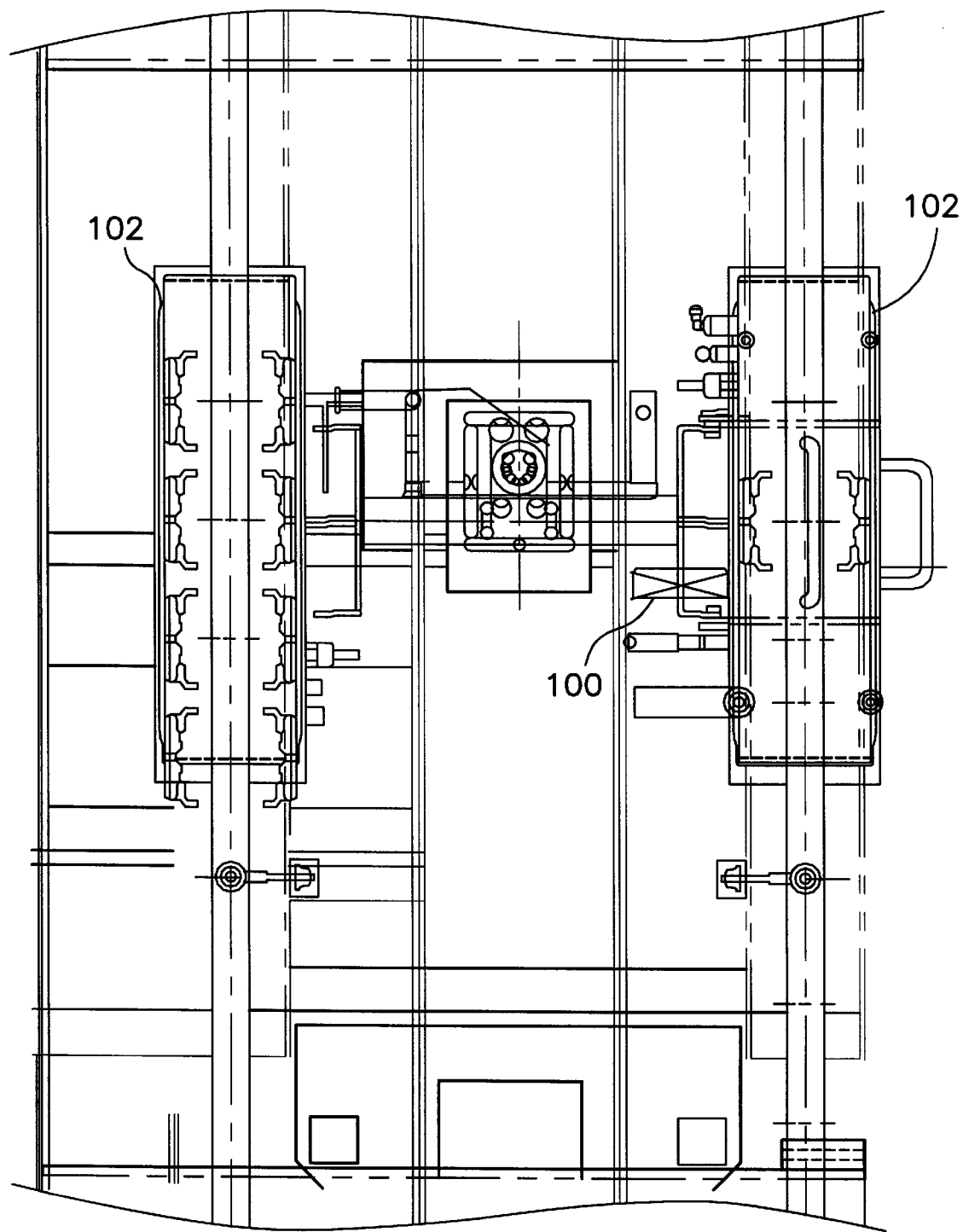
Figure 9:
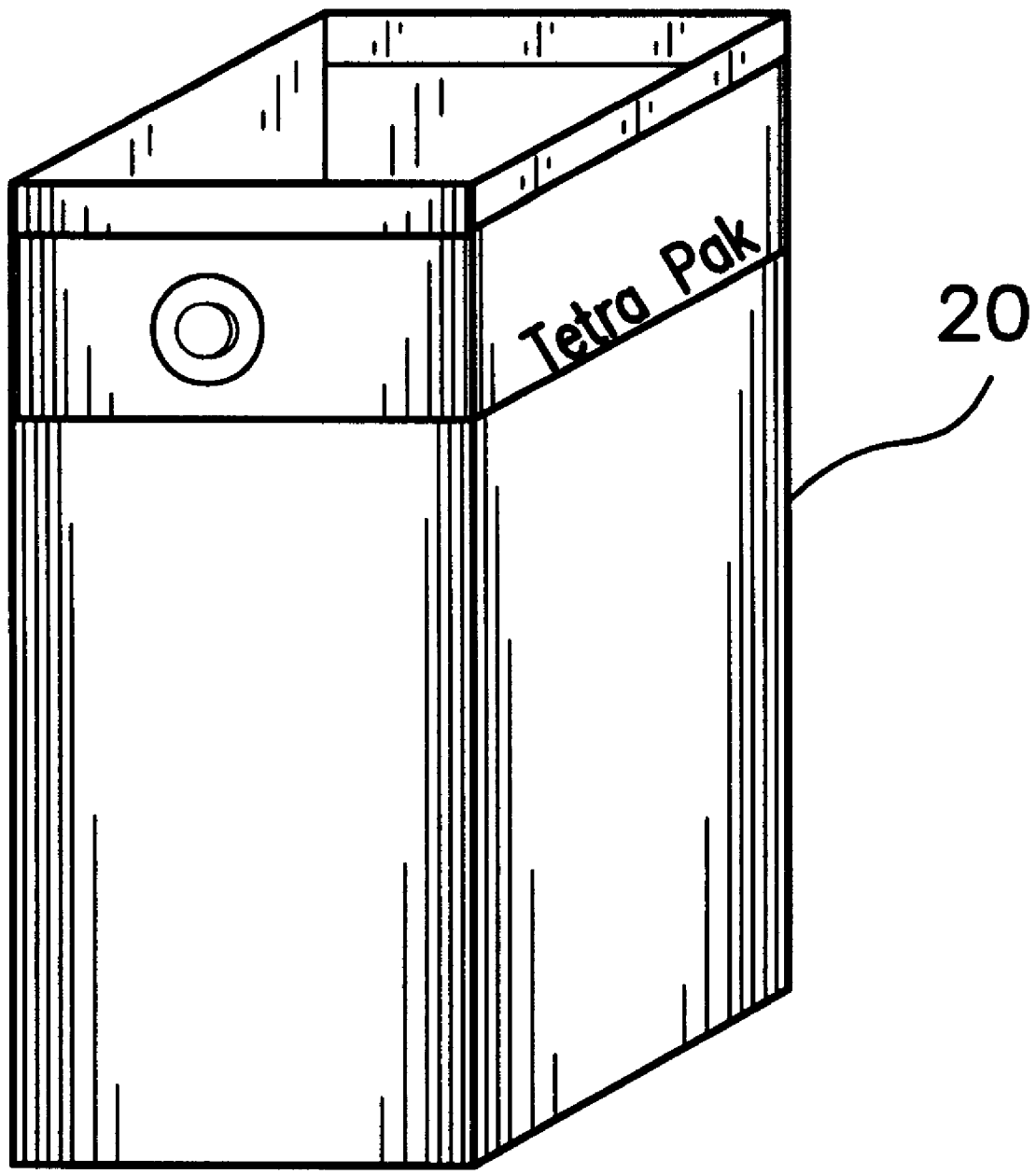

There is illustrated in FIG. 2 chematic flow diagram of the ignitor connection to the ultraviolet lamp of the present invention;

There is illustrated in FIG. 3 a graph of incoming voltage supplied to a power supply;

There is illustrated in FIG. 4 a graph of voltage from a power supply to a UV lamp in the prior art;

There is illustrated in FIG. 5 a graph of voltage of the present invention from a power supply to a UV lamp, the power supply having an ignitor;

There is illustrated in FIG. 6 a front cross-sectional view of an ultraviolet radiation chamber with the means for monitoring diposed thereon;

There is illustrated in FIG. 7 a top view of ultraviolet radiation chamber with the means for monitoring disposed thereon;

There is illustrated in FIG. 8 a schematic view of the monitoring device of the present invention;

There is illustrated in FIG. 9 a perspective view of a carton to be sterilized by the UV system of the present invention.

DETAILED DESCRIPTION OF THE INVENTION

Figure 1:
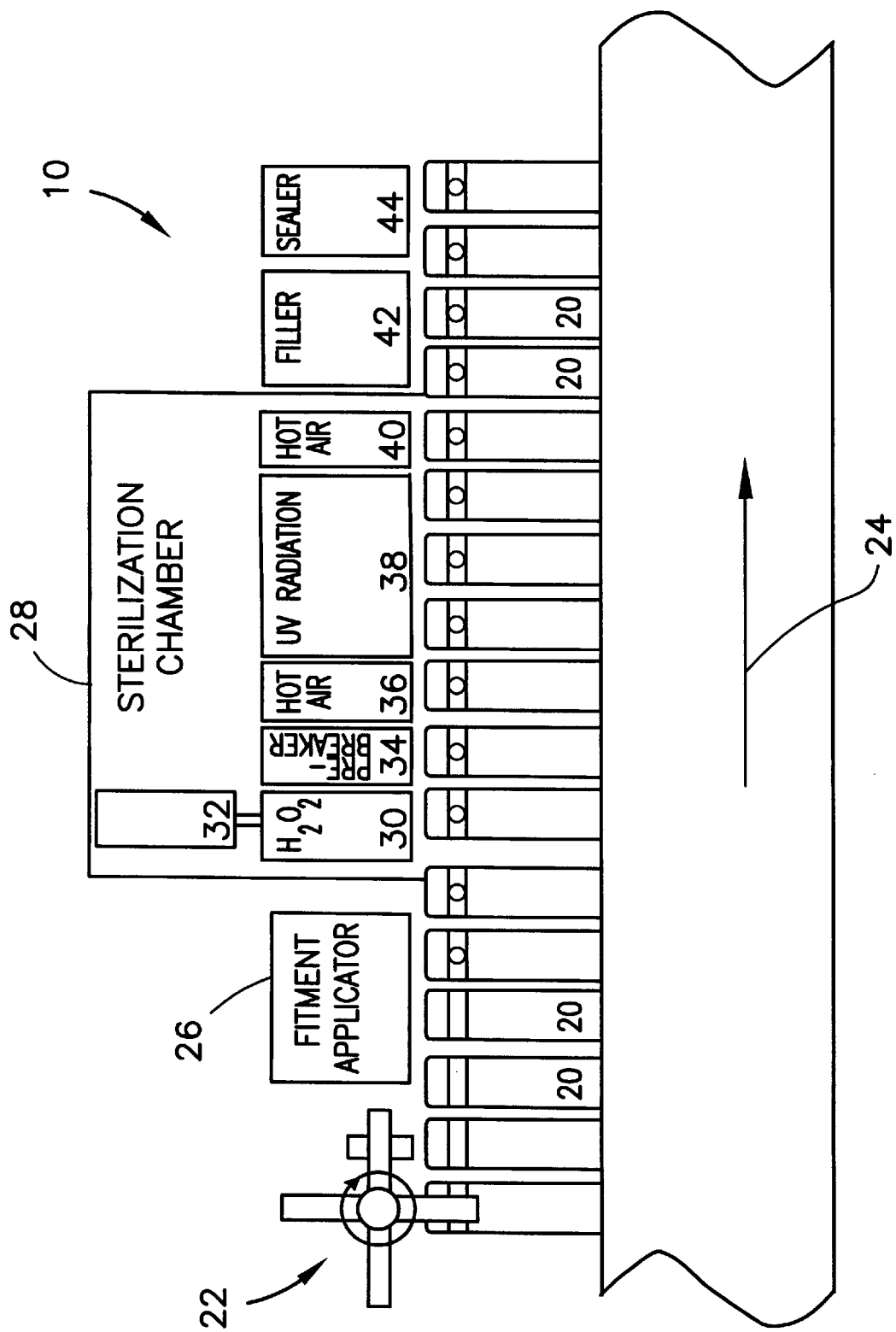

As shown in FIG. 1, a linear form, fill and seal packaging machine 10 is composed of several stations. A mandrel wheel 22 for forming the bottom of a carton 20 is placed near the beginning of a conveyor line 24. After the mandrel wheel 22, each carton of a series of cartons 20 is placed on the conveyor line 24 for transport to the next station which might be a fitment applicator station 26. Downline from the fitment applicator station 26 is the sterilization chamber 28 which may have a sterilant applying sub-station 30 connected to a supply of sterilant 32, a pre-breaker sub-station 34, a hot air sub-station 36, an ultraviolet radiation sub-station 38, and a second hot air sub-station 40. Subsequent to the sterilization station is a filling station 40 followed by a sealing station 44. An exemplary machine is a TETRA REX® machine available from Tetra Pak, Inc. of Chicago, Ill.

As shown in FIG. 2, an ignitor 50 is disposed between a power supply 52 and the ultraviolet lamp 54. The ignitor 50 delivers a high voltage to the ultraviolet lamp 54 decreasing the start-up and re-start time for the ultraviolet lamp 54. The ultraviolet lamp may be a medium pressure mercury lamp which emits ultraviolet radiation primarily in the 254 nanometer wavelength. The starting of the UV lamp is defined as providing sufficient voltage for a voltage spike to strike an arc in the UV lamp 54. Once the UV lamp 54 is struck, the UV lamp 54 is activated and the ignitor 50 has completed its task. The starting of the UV lamp 54 should occur within a few milliseconds. The normal voltage delivered to the UV lamp 54 is 320–360 volts which heats the lamp 54 to an operating temperature of 600° C. within five minutes. However, in a cold environment this voltage would be inadequate to strike an arc in the UV lamp. On the ignitor 50, the "D" connection is the ballast connection, the "L" connection is the line connection, and the "N" connection is the neutral connection.

As shown in FIG. 3, the voltage delivered to the power supply 52 is approximately 230 volts, in an alternating current at 50 Hz. FIG. 4 is the prior art, and shows the outgoing voltage from the power supply to a UV lamp at approximately 450 volts, in an alternating current at 50 Hz. The voltage flows as a sine curve for each one Hertz. In a cold environment, below 8° C., the prior art voltage would be inadequate to strike an arc across a UV lamp, such as UV lamp 54. During initial commencement of the UV lamp, the cold temperature has a volume/pressure reducing effect on the inert gas within the shell of a UV lamp, which prevents the striking of an arc across the UV lamp. Alternatively, if an UV lamp must be deactivated in order to resolve a problem on the packaging machine, the operator must wait for the UV lamp to cool down in order to strike an arc across the UV lamp. The cool down period allows a sufficient amount of the vapor phase mercury to condense.

FIG. 5 illustrates the voltage from the power supply 52 to the UV lamp 54 via the ignitor 50. The ignitor 50 delivers up to 4000 volts to the lamp 54 which will strike an arc where the previously used 450 volts peak will not strike an arc. The initial spike, up to 4000 volts, allows for an arc to be struck whether the UV lamp is cold (during initial commencement) or after a line shutdown (when the UV lamp is hot and the mercury is in the vapor phase). The ignitor amplifies the voltage delivered to the power supply 52 thus delivering the high voltage to the UV lamp 54. Such an ignitor is the PARMAR PT150 ignitor, capable of 6000 volts pulses, available from PARRY. The reciprocal relationship between temperature and amount of voltage necessary to create an arc across an UV lamp necessitates such an ignitor in the coldest environments. As the temperature decreases, a greater voltage is necessary to strike an arc across an UV lamp 54. The 4000 volts of the ignitor is sufficient for most cold environments, however, it is well within the scope of the present invention to provide an ignitor 50 which is capable of delivering an even greater voltage.

As shown in FIGS. 6 and 7, a set of monitoring devices 100 are disposed in relation to a ultraviolet lamp 54 mounted above a conveyor line 24. An open-ended carton 20 is conveyed under the lamp 54 for irradiation thereof. As mentioned previously, the intensity of ultraviolet energy must be sufficient to adequately sterilize the container for filling and sealing further down the line 24. One preferred target dose for sterilizing a carton is 32 mW/cm$^2$-sec. The ultraviolet lamp 54 may be maintained within a moveable hood 102. Each monitor 100 is positioned so as to receive the same intensity of radiation directed to a carton 20 being irradiated below on the conveyor line 24.

As shown in FIG. 8, the monitoring device 100 receives ultraviolet radiation, shown as beam of light 104, directly from the ultraviolet lamp 54. The beam of light 104 is transmitted through an ultraviolet transparent window 106. The beam of light 104 is then reflected from a first mirror 108 to a second mirror 110 then reflected again to a photodiode and amplifier 112. It should be obvious to those skilled in the pertinent art that the angle of reflection from both mirrors 108 and 110 may be modified to direct the beam of light 104 to the photodiode 112.

The intensity of the ultraviolet radiation is measured by the photodiode and amplifier 112 and a signal may be transmitted to a PLC which can be adapted to analyze the information and indicate any change in the intensity. The indication from the PLC may be an audible or visual warning to the operator of the packaging machine 10. The window may also have an automatic cleaning mechanism to prevent interference with the transmission of the beam of light 104 therethrough.

In operation, each of a series of blanks is erected into a partially-formed cartons prior to transport to the sterilization station shown in FIG. 1. The blanks have their top open for access to the interior of the carton 20, as shown in FIG. 9. When each of the series of cartons reaches the sterilization station, a sterilant, if use, is introduced into the interior of the carton. The carton, with or without sterilant, is transported to the UV lamp 54. Radiation emitted by the UV lamp irradiates the interior of the carton 20 in order to sterilize the carton 20 prior to filling with a desired product at the filling station. In this manner, a sterilized container is provided for the product which results in a longer shelf-life for the product depending on the type of product, and whether or not the product is refrigerated or not. The UV system of the present invention allows for the facilitated and safe production of cartons containing various products.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes, modifications and substitutions of equivalents may be made therein without departing from the spirit and scope of this invention which is intended to be unlimited by the foregoing except as may appear in the following appended claims. therefore, the embodiments of the invention in which an exclusive property or privilege is claimed are defined in the following appended claims.

I claim as my invention:

1. An ultraviolet sterilization system integrated within a linear form, fill and seal packaging machine, the packaging machine processing a series of containers along a linear path, the ultraviolet sterilization system comprising:

an ultraviolet lamp disposed above the linear path of the series of containers to thereby irradiate each of the series of containers;

a power supply for providing voltage to the ultraviolet lamp in order to activate the ultraviolet lamp;

an ignitor in voltage communication with the ultraviolet lamp and the power supply, the ignitor providing a higher voltage to the ultraviolet lamp for activation of the ultraviolet lamp under conditions which would prevent activation of the ultraviolet lamp with only voltage from the power supply; and a monitor adapted to monitor the intensity of the ultraviolet lamp for changes in a predetermined intensity of the ultraviolet lamp, the monitor including an enclosed cavity mounted in relation to the ultraviolet lamp, the enclosed cavity having a window transparent to the transmission of ultraviolet radiation from the ultraviolet lamp and a photodiode disposed within the enclosed cavity, the photodiode configured to sense a portion of the ultraviolet radiation transmitted through the window.

2. The ultraviolet sterilization system according to claim 1 wherein the ignitor delivers a voltage of 4000 volts to the ultraviolet lamp within twenty milliseconds.

3. The ultraviolet sterilization system according to claim 1 wherein the ultraviolet lamp is heated to a temperature of 600° C. within five minutes.

4. The ultraviolet sterilization system according to claim 1 wherein the ignitor creates an arc across the ultraviolet lamp in temperature as low as 0° C.

5. The ultraviolet sterilization system according to claim 1 wherein the ultraviolet lamp is a medium pressure mercury lamp.

6. The ultraviolet sterilization system according to claim 1 further comprising indication for alerting an operator of a change in the intensity of ultraviolet energy.

7. The ultraviolet sterilization system according to claim 1 wherein the monitor includes first and second mirrors within the enclosed cavity, the first mirror positioned to receive and reflect ultraviolet radiation transmitted through the window to the second mirror, and wherein the second mirror is positioned to reflect ultraviolet radiation from the first mirror to the photodiode.

* * * * *